United States Patent
Felt et al.

(10) Patent No.: US 6,248,131 B1
(45) Date of Patent: *Jun. 19, 2001

(54) ARTICULATING JOINT REPAIR

(75) Inventors: Jeffrey C. Felt, Greenwood; Craig A. Bourgeault; Matthew W. Baker, both of Minneapolis, all of MN (US)

(73) Assignee: Advanced Bio Surfaces, Inc., Minnetonka, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/925,838

(22) Filed: Sep. 5, 1997

Related U.S. Application Data

(63) Continuation-in-part of application No. 08/590,293, filed on Jan. 23, 1996, now Pat. No. 5,888,220, and a continuation-in-part of application No. 08/239,248, filed on May 6, 1994, now Pat. No. 5,556,429.

(51) Int. Cl.⁷ ....................................................... A61F 2/44

(52) U.S. Cl. ........................................... 623/17.12; 606/61

(58) Field of Search ............................ 623/66, 16, 17.12, 623/17.16; 606/86–88, 92–94, 61

(56) References Cited

U.S. PATENT DOCUMENTS

| Re. 29,345 | 8/1977 | Erb . |
|---|---|---|
| 3,320,131 | 5/1967 | Smith . |
| 3,875,595 | 4/1975 | Froning . |
| 4,368,040 | 1/1983 | Weissman . |
| 4,446,578 | 5/1984 | Perkins et al. . |
| 4,570,270 | 2/1986 | Oechsle, III . |

(List continued on next page.)

FOREIGN PATENT DOCUMENTS

| 0505634 | 4/1991 | (EP) . |
|---|---|---|
| 2639823 | 12/1988 | (FR) . |
| WO9311723 | 6/1993 | (WO) . |

OTHER PUBLICATIONS

Adamus, Dan, "Polycarbonate Inflation Devices Simplify Balloon Angioplasty".

Bao, Qi–Bin et al., "Review: The artificial disc: theory, design and materials", *Biomaterials* 17:(12):1157–1167 (1996).

DeLong, W.B., "Microsurgical Discectomy and Spinal Decompression", 75:1029–1045.

Erb, R., et al, "Hysteroscopic Oviductal Blocking with Formed–in–Place Silicone Rubber Plugs", *Journal of Reproductive) Medicine*, 23:65–68 (1979.

Garcia, A., "Intradiscal Polymerization: Preliminary Results of Chemical and Biomechanical Studies", *The Artificial Disc* (1991).

Kambin, P., "Arthroscopic Microdiscectomy: Lumbar and Thoracic", 73: 1002–1015.

T.P. Reed et al., "Tubal Occlusion with Silicone Rubber", J. Reprod. Medicine, vol. 25, No. 1, Jul. 1980, pp. 25–28.

Regan, J., et al, "Atlas of Endoscopic Spine Surgery", pp. 338–345.

(List continued on next page.)

*Primary Examiner*—Bruce Snow
(74) *Attorney, Agent, or Firm*—Fredrikson & Byron, P.A.

(57) ABSTRACT

A method and related materials and apparatus for using minimally invasive means to repair (e.g., reconstruct) tissue such as fibrocartilage, and particularly fibrocartilage associated with diarthroidal and amphiarthroidal joints. The method involves the use of minimally invasive means to access and prepare damaged or diseased fibrocartilage within the body, and to then deliver a curable biomaterial, such as a two-part polyurethane system, to the prepared site, and to cure the biomaterial in situ in order to repair the fibrocartilage. Applications include repair and replacement of the intervertebral disc of the spine.

6 Claims, 1 Drawing Sheet

U.S. PATENT DOCUMENTS

| | | |
|---|---|---|
| 4,651,736 | 3/1987 | Sanders . |
| 4,772,287 | 9/1988 | Ray et al. . |
| 4,863,477 | 9/1989 | Monson . |
| 4,904,260 | 2/1990 | Ray et al. . |
| 4,913,701 | 4/1990 | Tower . |
| 4,932,969 | 6/1990 | Frey et al. . |
| 4,969,888 | 11/1990 | Scholten et al. . |
| 5,002,576 | 3/1991 | Fuhrmann et al. . |
| 5,067,964 | 11/1991 | Richmond et al. . |
| 5,078,720 | 1/1992 | Burton et al. . |
| 5,108,404 | 4/1992 | Scholten et al. . |
| 5,171,280 | 12/1992 | Baumgartner . |
| 5,258,028 | 11/1993 | Ersek et al. . |
| 5,290,306 | 3/1994 | Trotta et al. . |
| 5,334,201 | 8/1994 | Cowan . |
| 5,342,305 | 8/1994 | Shonk . |
| 5,344,444 | 9/1994 | Glastra . |
| 5,344,459 | 9/1994 | Swartz . |
| 5,376,064 | 12/1994 | Cerny . |
| 5,385,469 | 1/1995 | Weissman . |
| 5,411,477 | 5/1995 | Saab . |
| 5,458,643 | 10/1995 | Oka et al. . |
| 5,470,314 | 11/1995 | Wallinsky . |
| 5,529,653 | 6/1996 | Glastra . |
| 5,545,229 | 8/1996 | Parsons et al. . |
| 5,549,679 | 8/1996 | Kuslich . |
| 5,556,429 * | 9/1996 | Felt .......................................... 623/16 |
| 5,562,736 * | 10/1996 | Ray et al. . |
| 5,571,189 | 11/1996 | Kuslich . |
| 5,591,199 | 1/1997 | Porter et al. . |
| 5,645,597 | 7/1997 | Krapiva . |
| 5,888,220 * | 3/1999 | Felt et al. ................................. 623/17 |

OTHER PUBLICATIONS

Roy–Camille, R., et al., "Experimental Study of Lumbar Disc Replacement", SO.F.C.O.T. Annual Meeting, Nov. 1977, Suppl. II, *Rev. Chir. Orthop.* 64, 1978. (uncertified translation).

Simmons, J. et al., "Posterior Lumbar Interbody Fusion: Biomechanical Selection for Fusions", 81:1100–1111 (1995).

A. Takahara, et al., "Effect of Soft Segment Chemistry on the Biostability of Segmented Polyurethanes. II. In vitro 1991 Hydrolytic Degradation and Lipid Sorption", *J. Biomedical Materials Research*, 26:801–818 (1992).

A. Takahara, et al., "Effect of Soft Segment Chemistry on the Biostability of Segmented Polyurethanes. I. In vitro Oxidation", *J. Biomedical Materials Research*, 25:341–356 (1991).

"Guide to Medical Plastics", pp. 41–78 in *Medical Device & Diagnostic Industry*, Apr., 1994.

\* cited by examiner

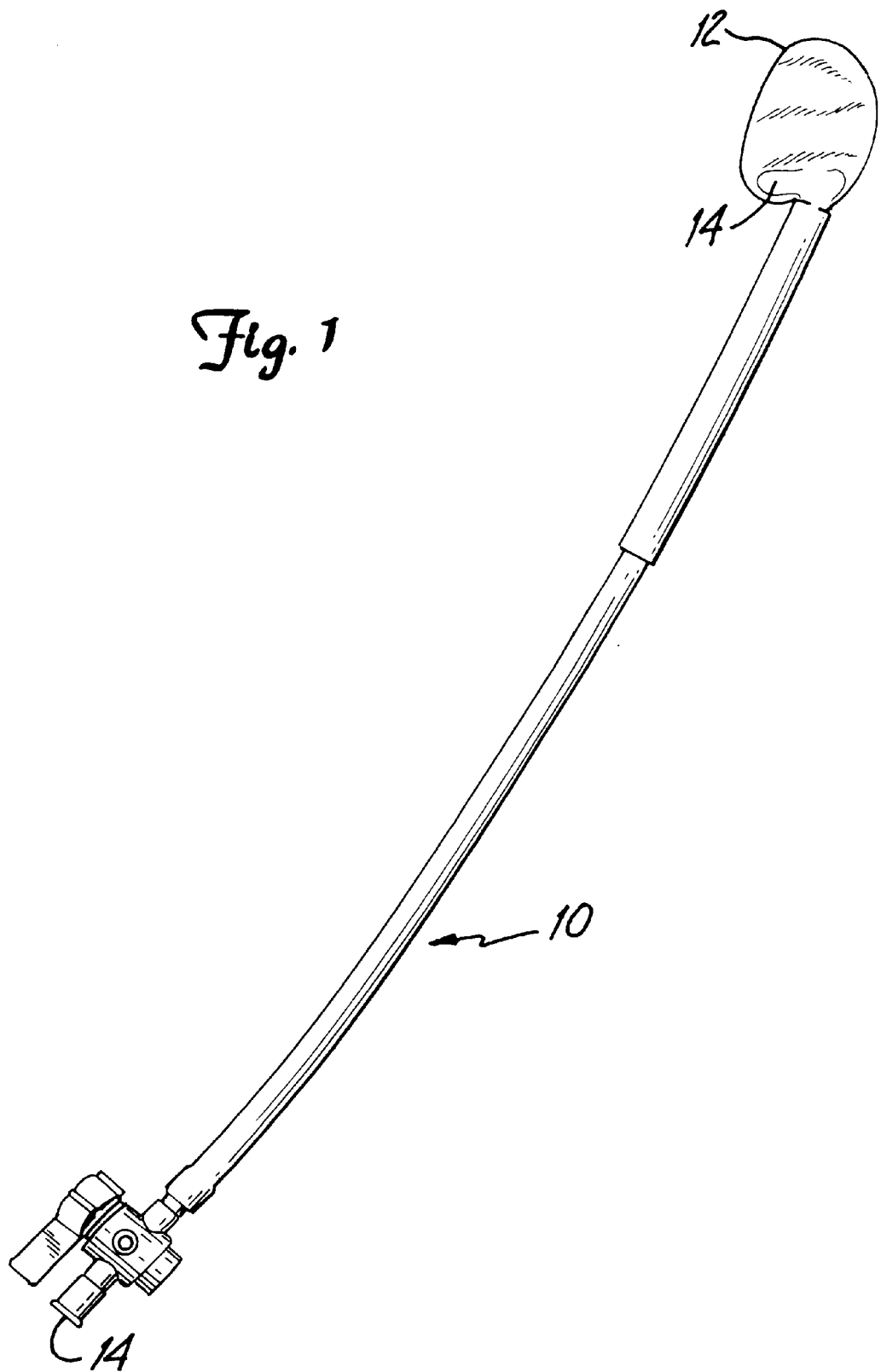

ARTICULATING JOINT REPAIR

CROSS-REFERENCE TO RELATED APPLICATIONS

This application is a divisional of U.S. application Ser. No. 08/590,293, filed Jan. 23, 1996 for JOINT RESURFACING SYSTEM now U.S. Pat. No. 5,888,220 which is a continuation-in-part of U.S. Ser. No. 08/239,248, filed May 6, 1994, now U.S. Pat. No. 5,556,429.

TECHNICAL FIELD

The present invention relates to methods, apparatuses, materials and systems for the repair of movable and mixed articulating joints in the body.

BACKGROUND OF THE INVENTION

The joints of the body can be classified as between those that provide immovable articulations (synarthroidal), mixed articulations (amphiarthroidal), and movable articulations (diarthroidal). The ability of amphiarthroidal and diarthroidal joints to provide effective and pain-free articulation, and/or to serve their weight-bearing function, is generally dependent on the presence of intact, healthy fibrocartilage within the joint.

In an amphiarthroidal joint such as the lumbar joint of the back, the vertebra are separated by an intervertebral disc formed of fibrocartilage. More particularly, the intervertebral disc is comprised of an outer annulus fibrosis formed of fibrocartilage. The annulus, in turn, surrounds and contains a more fluid material known as the nucleus pulposus. By virtue of its fluidity, the nucleus allows for both movement and weight-bearing energy transfer. In healthy, generally younger individuals, the annulus is intact and the nucleus pulposus remains quite fluid.

As people age, however, the annulus tends to thicken, desiccate, and become more rigid. The nucleus pulposus, in turn, becomes more viscous and less fluid and sometimes even dehydrates and contracts. The annulus also becomes susceptible to fracturing or fissuring. These fractures tend to occur all around the circumference of the annulus, and can extend from both the outside of the annulus inward, and from the interior outward. Occasionally, a fissure from the outside will meet a fissure from the inside and will result in a complete rent through the annulus fibrosis. In a situation like this, the nucleus pulposus may extrude out through the intervertebral disc. The extruded material, in turn, can impinge on the spinal cord or on the spinal nerve rootlets as they exit through the intervertebral foramen, resulting in the symptoms associated with the classic "ruptured disc".

The current surgical approach to treating a degenerated intervertebral disc generally involves the process of microdiscectomy, in which the site is accessed and the protruded material is removed. This often produces significant relief, provided it is a fairly minor, or mild, localized disc protrusion. In such a procedure a small incision is made, through which the disc is visualized. The area of protruded material is removed, thus decompressing the nerve rootlet that has been impinged on by the extruded material.

In more severe situations, however, the annulus fibrosis becomes degenerated to the point where very little disc space remains, and much of the nucleus pulposus is either contracted or has been extruded. Regional osteophytes can also develop around these areas. The combination of the extruded material and the osteophytes, together with the narrowing of the intervertebral disc space produces a marked narrowing of the intervertebral foramen and impingement on the spinal nerve rootlet as it exits the canal. This is the classical situation that results in radicular pain with axial loading.

When this occurs it becomes necessary to reestablish the intervertebral space. The current approach to this more severe situation is a lumbar laminectomy (to decompress the nerve rootlet) with fusion of the disc space. The bony lamina is removed to decompress the intervertebral foramina and the bone graft is taken from the anterior iliac crest and attached from one vertebrae body to the next. The resulting fusion will maintain stability at that point and also help maintain the separation of the vertebrae.

Recent advances in this technology have been developed by such companies as Spine-Tech, Minneapolis, Minn., which involves the use of a titanium alloy cylinder. The cylinder is screwed into the intervertebral space to assure the stability of the spacing until a fully bony ankylosis can be obtained. The cylinders are packed with bone and are fenestrated so that the packed bone can grow out into the adjacent vertebrae and solidify the fusion. To date, however, clinical results on the long-term follow up of these patients are not available and the efficacy is still in doubt with many spine surgeons.

It would therefore be particularly useful to be able to repair such injuries in a manner that avoids invasive surgical procedures and the problems associated therewith.

SUMMARY OF THE INVENTION

The present invention provides a method and related materials and apparatus for using minimally invasive means to repair (e.g., reconstruct) tissue such as fibrocartilage, and particularly fibrocartilage associated with diarthroidal and amphiarthroidal joints. The method involves the use of minimally invasive means to access and prepare damaged or diseased fibrocartilage within the body, and to then deliver a curable biomaterial to the prepared site, and to cure the biomaterial in situ in order to repair the fibrocartilage. The cured biomaterial provides an optimal combination of such properties as deliverability and curability, as well as biocompatability, biostability, and such physical performance characteristics as strength, elasticity, and lubricity.

In one embodiment, the method comprises the steps of:
a) using minimally invasive means to remove damaged or diseased fibrocartilage from a diarthroidal or amphiarthroidal joint, and to create a mold capable of containing curable biomaterial in a desired position within the joint,
b) providing one or more curable biomaterials to the structure previously occupied by the removed fibrocartilage, and
c) curing the biomaterials in order to provide a replacement for the fibrocartilage.

The mold created within the joint is preferably of sufficient shape and dimensions to allow the resulting cured biomaterial to replace or mimic the structure and function of the removed fibrocartilage. The mold can be formed of synthetic and/or natural materials, including those that are provided exogenously and those provided by the remaining natural tissues. The mold can either be removed from the site, upon curing of the biomaterial, or is sufficiently biocompatible to allow it to remain in position.

The mold can take the form of either a positive and/or negative mold. For instance, the mold can take the form of an outer shell, capable of retaining biomaterial within its interior cavity. Optionally, the mold can also take any other suitable form, including to serve as an interior core (e.g., to create a doughnut shaped biomaterial), or as an anchor point for the stable attachment and localization of delivered biomaterial.

In a particularly preferred embodiment, the method is used to repair an amphiarthroidal joint such as an intervertebral disc and comprises the steps of:
a) using microsurgical techniques to perform a discectomy while preserving an outer annular shell,
b) providing one or more curable biomaterials to the interior of the annular shell, and
c) curing the biomaterials in order to provide a replacement disc.

In such a preferred embodiment, the distraction of the disc space is accomplished by means of a suitable distraction means, such as an inflatable, yet rigid, balloon or bladder. The balloon can be delivered in deflated form to the interior of the annulus and there inflated in order to distract the disc space and provide a region for the delivery of biomaterial. The balloon is preferably of sufficient strength and suitable dimensions to distract the space to a desired extent and for a period long enough for the biomaterial to be delivered and cured.

In other aspects, the invention provides biomaterials, including polymer systems, useful for performing such a method, as well as methods of preparing and using such biomaterials. In yet further aspects, the invention provides a diarthroidal or amphiarthroidal joint having interposed therein a biomaterial that has been cured in situ.

DETAILED DESCRIPTION

Applicants have discovered a means for producing spinal separation to achieve pain relief, which involves the step of interposing cured biomaterial in the intervertebral disc space.

Definitions

As used herein the following words and terms shall have the meanings ascribed below:

"repair" will refer to the use of a biomaterial to replace or provide some or all of the structure or function of natural tissue in vivo, for instance, to replace fibrocartilage present in a diarthroidal or amphiarthroidal joint. Repair can take any suitable form, e.g., from patching the tissue to replacing it in its entirety, preferably in a manner that reconstructs its native dimensions;

"biomaterial" will refer to a material that is capable of being introduced to the site of a joint by minimally invasive means, and there be cured to provide desired physical-chemical properties in vivo;

"cure" and inflections thereof, will refer to any chemical-physical transformation that allows a biomaterial to progress from a form (e.g., flowable form) that allows it to be delivered by minimally invasive means, to a more permanent form for final use in vivo. When used with regard to the method of the invention, for instance, "curable" can refer to uncured biomaterial, having the potential to be cured in vivo (as by the application of a suitable energy source), as well as to a biomaterial that is in the process of curing, as with a biomaterial formed at the time of delivery by the concurrent mixing of a plurality of biomaterial components;

"minimally invasive means" refers to surgical means, such as endoscopic or arthroscopic surgical means, that can be accomplished without the need to resect tissue in order to gain access to a site of orthopedic injury;

"endoscopic/arthroscopic surgical instrument" refers to the controllers and associated hardware and software necessary for performing conventional endoscopic or arthroscopic surgery; and "delivery cannula" shall mean a cannula capable of being operated in a minimally invasive fashion, e.g., under arthroscopic visualization, together with associated connective tubing and containers for the operable and fluid attachment of the cannula to a source of biomaterial for the storage, delivery, and recovery of biomaterials of the present invention.

Method

In a preferred embodiment, the present invention provides a method and related materials and apparatus for repairing diarthroidal and amphiarthroidal joints by minimally invasive means. The method involves the use of minimally invasive means to prepare the site of injury, deliver a curable biomaterial to the joint site, and to cure the biomaterial in situ in order to repair fibrocartilage.

The method of the invention can be used to repair a number of tissues, including a variety of joints, and is particularly useful for diarthroidal and amphiarthroidal joints. Examples of suitable amphiarthroidal joints include the synphysoidal joints, such as the joints between bodies of the vertebrae. Such joints provide surfaces connected by fibrocartilage, and have limited motion. Other examples include syndesmoidal joints, having surfaces united by an interosseous ligament, as in the inferior tibio-fibular joint.

Examples of suitable diarthroidal joints include the ginglymus (a hinge joint, as in the interphalangeal joints and the joint between the humerus and the ulna); throchoides (a pivot joint, as in superior radio-ulnar articulation and atlanto-axial joint); condyloid (ovoid head with elliptical cavity, as in the wrist joint); reciprocal reception (saddle joint formed of convex and concave surfaces, as in the carpo-metacarpal joint of the thumb); enarthrosis (ball and socket joint, as in the hip and shoulder joints) and arthrodia (gliding joint, as in the carpal and tarsal articulations).

In a particularly preferred embodiment, the method is used to repair an amphiarthroidal joint such as an intervertebral disc and comprises the steps of:
a) using microsurgical techniques to perform a discectomy while preserving an outer annular shell,
b) providing a curable biomaterial to the annular shell, and
c) curing the polymer in order to provide a replacement disc.

As can be seen, the annular shell can itself serve as a suitable mold for the delivery and curing of biomaterial. Optionally, the interior surface of the annular shell can be treated or covered with a suitable material in order to enhance its integrity and use as a mold. Preferably, one or more inflatable devices, such as the balloons described herein, can be used to provide molds for the delivery of biomaterials. More preferably, the same inflatable devices used to distract the joint space can further function as molds for the delivery and curing of biomaterial.

Discectomy

A discectomy (i.e., removal of some or all of the nucleus pulposis, leaving an outer annular shell) is performed, with optional distraction and repair of the annulus, in order to remove the destroyed nucleus material while providing an intact annular shell. By "intact", it is meant that the annulus, either alone or with optional supporting means, is of sufficient strength and integrity to retain a biomaterial in a desired position and in the course of its use (delivery and curing).

The microsurgery for the intervertebral disc polymer placement can be carried out using techniques well within the skill of those in the art, given the present teaching. The annulus can be viewed, for instance, using a laser or endoscope. The integrity of the annular shell is assessed, and optionally, the shell itself is repaired, e.g., by the application of a biocompatible patching material, such as a fibrin glue.

The destroyed disc material is cleaned out and the annulus is cleaned out to the edges of the annulus. The annular shell, including any repaired portions are preferably of sufficient strength and dimensions to allow the biomaterial to be delivered and cured. The remaining, repaired annulus then serves as an outer barrier for the curable biomaterial, thereby serving to provide accurate dimensions and location for the cured biomaterial.

Once the nucleus pulposis has been removed and the remaining annulus repaired, the annular shell can itself be used as an envelope to contain the delivered biomaterial. Optionally, and preferably, means are provided to contain the biomaterial within the desired space, e.g., by forming an additional envelope within the annulus.

As used herein the word "distraction", and inflections thereof, will refer to the separation of joint surfaces to a desired extent, without rupture of their binding ligaments and without displacement. Distraction can be accomplished by any suitable means. Such means include mechanical means and hydrostatic means, e.g., by pressurized injection of the biomaterial itself. By the use of distraction, the disc space can be sufficiently re-established to achieve any desired final dimensions and position. Optionally, and preferably, the means used to accomplish distraction also serve the purpose of forming one or more barriers (e.g., envelopes) for the uncured biomaterial itself.

The disc space can be distracted prior to and/or during either the discectomy itself and/or delivery of biomaterial. A constricted disc space is generally on the order of 3 to 4 mm in length. Suitable distraction means are capable of providing on the order of about 3 atmospheres to about 4 atmospheres, (or on the order of about 40 psi to about 60 psi) in order to distract that space to on the order of 8 to 12 mm in length.

Distraction can be accomplished by any suitable means, including by mechanical and/or hydrostatic means. Mechanical means can include, for instance, attaching hooks or jacks to the bony endplates and using those hooks or jacks to separate the bones. Optionally, the surgeon can employ external traction, however, with the patient on their side, external traction will likely not be preferred.

Optionally, and preferably, the space is distracted by the use of one or more suitable insertable devices, e.g., in the form of inflatable balloons. When inflated, such balloons provide rigid walls (e.g., fiber supported) that are sufficiently strong to distract the space. An inflatable device provides sufficient strength and dimensions can be prepared using conventional materials. In use, the uninflated balloon can be delivered to the center of the annular shell, and there inflated to expand the annular shell and in turn, distract the space.

The inflatable device can be delivered to the disc space by any suitable means, e.g., in deflated form retained within or upon the end of a rigid or semi-rigid rod. Once positioned within the disc, generally centrally within the annular shell, a suitable gas (e.g., nitrogen or carbon dioxide) can be delivered through the rod in order to inflate the balloon in situ, in a substantially radial direction. The fact that the balloon is properly placed can be confirmed by the use of ancillary means, such as cine using a C arm, or by self-effecting means embodied within the balloon itself or its delivery apparatus.

Suitable materials for preparing balloons of the present invention are those that are presently used for such purposes as balloon angioplasty. Suitable materials provide an optimal combination of such properties as compliance, biostability and biocompatability, and mechanical characteristics such as elasticity and strength. Balloons can be provided in any suitable form, including those having a plurality of layers and those having a plurality of compartments when expanded. A useful balloon apparatus will include the balloon itself, together with a delivery catheter (optionally having a plurality of lumen extending longitudinally therewith), and fluid or gas pressure means.

Examples of suitable materials (e.g., resins) for making balloons include, but are not limited to, polyolefin copolymers, polyethylene, polycarbonate, and polyethylene terephthalate. Such polymeric materials can be used in either unsupported form, or in supported form, e.g., by the integration of dacron or other fibers.

Balloons can also take several forms, depending on the manner in which the biomaterial is to be delivered and cured. A single, thin walled balloon can be used, for instance, to contact and form a barrier along the interior surface of the remaining annular material. Once positioned, one or more curable biomaterials can be delivered and cured within the balloon to serve as a replacement for the removed material. In such an embodiment, the balloon is preferably of a type that will allow it to remain in position, without undue detrimental effect, between the annular material and the cured biomaterial.

Optionally, a balloon can be provided that fills less than the entire volume of the annular shell. In such an embodiment, the balloon can be, for instance, in the shape of a cylinder. Such a balloon can be provided such that its ends can be positioned to contact the opposing vertebral bodies, and its walls will provide sufficient strength to cause distraction of the space upon inflation.

Thereafter, a first biomaterial is delivered to perimeter of the annular space, i.e., the space between the annular material and the balloon, and there cured. The biomaterial is delivered using suitable means, and under conditions suitable to ensure that it will not extrude through tears in the annulus. Optionally, the balloon can be gradually deflated as additional biomaterial is inserted into the space.

With the outer biomaterial cured in place, the balloon can be removed and an additional biomaterial, of either the same or a different type, can be delivered and cured in whatever remaining space was previously occupied by the balloon. A second cannula can be used to deliver a second biomaterial, preferably one that cures to provide a more flexible region that more closely approximates the physical characteristics of the original nucleus. This method provides the option to reconstruct the disc in a manner that more closely approximates the overall physical characteristics and relationship of the original annulus and nucleus.

A two step approach, as described above, is preferred for a number of reasons. It provides the means for distracting the joint, while at the same time facilitating the preparation of a final reconstructed annulus having two or more regions. The different regions, i.e., a rigid outer shell in combination with a more liquid interior, can provide a function that mimics that of the native disc. In addition to a two step approach, however, an implant having a plurality of regions, can be provided by other means as well. For instance, such an implant can be provided by the delivery of a single biomaterial that is cured to a greater or differing extent in its outermost, as compared to innermost, regions. An implant having a plurality of regions, or even a continuum of properties, is particularly preferred.

FIG. 1 shows a preferred mold apparatus of the invention, including a delivery cannula (10) and a balloon (12), the balloon capable of being positioned within an intervertebral disc space and there filled with biomaterial (14) delivered through cannula (10) in order to distract the space and cure in situ to provide a permanent replacement for the disc.

Biomaterials

Natural cartilage is a non-vascular structure found in various parts of the body. Articular cartilage tends to exist as a finely granular matrix forming a thin incrustation on the surfaces of joints. The natural elasticity of articular cartilage enables it to break the force of concussions, while its smoothness affords ease and freedom of movement. In terms of thickness, cartilage tends to take on the shape of the articular surface on which it lies. Where this is convex, the cartilage is thickest at the center, where the greatest pressure is received. The reverse is generally true in the case of concave articular surfaces.

Preferred biomaterials, therefore, are intended to mimic many of the physical-chemical characteristics of natural cartilage. Biomaterials can be provided as one component systems, or as two or more component systems that can be mixed prior to or during delivery, or at the site of repair. Generally such biomaterials are flowable in their uncured form, meaning they are of sufficient viscosity to allow their delivery through a cannula of on the order of about 2 mm to about 6 mm inner diameter, and preferably of about 3 mm to about 5 mm inner diameter. Such biomaterials are also curable, meaning that they can be cured or otherwise modified, in situ, at the tissue site, in order to undergo a phase or chemical change sufficient to retain a desired position and configuration.

When cured, preferred materials can be homogeneous (i.e., providing the same chemical-physical parameters throughout), or they can be heterogeneous. An example of a heterogeneous biomaterial for use as a disc replacement is a biomaterial that mimics the natural disc by providing a more rigid outer envelope (akin to the annulus) and an more liquid interior core (akin to the nucleus). In an alternative embodiment, biomaterials can be used that provide implants having varying regions of varying or different physical-chemical properties. With disc replacement, for instance, biomaterials can be used to provide a more rigid, annulus-like outer region, and a more fluid, nucleus-like core. Such di-or higher phasic cured materials can be prepared by the use of a single biomaterial, e.g., one that undergoes varying states of cure, or a plurality of biomaterials.

Common polymeric materials for use in medical devices include, for example, polyvinyl chlorides, polyethylenes, styrenic resins, polypropylene, thermoplastic polyesters, thermoplastic elastomers, polycarbonates, acrylonitrile-butadiene-styrene ("ABS") resins, acrylics, polyurethanes, nylons, styrene acrylonitriles, and cellulosics. See, for example, "Guide to Medical Plastics", pages 41–78 in *Medical Device & Diagnostic Industry,* April, 1994, the disclosure of which is incorporated herein by reference.

Suitable biomaterials for use in the present invention are those polymeric materials that provide an optimal combination of properties relating to their manufacture, application, and in vivo use. In the uncured state, such properties include processability, and the ability to be stably sterilized and stored. In the course of applying such material, such properties as flowability, moldability, and in vivo curability. In the cured state, such properties include cured strength (e.g., tensile and compressive), stiffness, biocompatability and biostability. Examples of suitable biomaterials include, but are not limited to, polyurethane polymers.

In a preferred embodiment, the biomaterial comprises a polyurethane polymer. Polyurethanes, e.g, thermoplastic polyurethanes ("TPU"), are typically prepared using three reactants: an isocyanate, a long-chain macrodiol, and a short-chain diol extender. The isocyanate and long-chain diol form a "soft" segment, while the isocyanate and short-chain diol form a "hard" segment. The hard segments form ordered domains held together by hydrogen bonding. These domains act as cross-links to the linear chains, making the material similar to a cross-linked rubber. It is the interaction of soft and hard segments that determines and provides the polymer with rubber-like properties.

Those skilled in the art, in view of the present invention, will appreciate the manner in which the choice of isocyanate, macrodiol, and chain extender can be varied to achieve a wide array of properties. Preferred TPU's for medical use are presently based on the use of a diisocyanate such as diphenylmethane diisocyanate ("MDI"), a glycol such as polytetramethylene ether glycol, and a diol such as 1,4-butanediol.

Biomaterials of the present invention can also include other optional adjuvants and additives, such as stabilizers, fillers, antioxidants, catalysts, plasticizers, pigments, and lubricants, to the extent such optional ingredients do not diminish the utility of the composition for its intended purpose.

When cured, the biomaterials demonstrate an optimal combination of physical/chemical properties, particularly in terms of their conformational stability, dissolution stability, biocompatability, and physical performance, e.g., physical properties such as density, thickness, and surface roughness, and mechanical properties such as load-bearing strength, tensile strength, shear strength, fatigue, impact absorption, wear characteristics, and surface abrasion. Such performance can be evaluated using procedures commonly accepted for the evaluation of natural tissue and joints, as well as the evaluation of biomaterials.

In particular, preferred biomaterials, in the cured form, exhibit mechanical properties that approximate those of the natural tissue that they are intended to replace. For instance, for load bearing applications, preferred cured composites exhibit a load bearing strength of between about 50 and about 200 psi (pounds per square inch), and preferably between about 100 and about 150 psi. Such composites also exhibit-a shear stress of between about 10 and 100 psi, and preferably between about 30 and 50 psi, as such units are typically determined in the evaluation of natural tissue and joints.

Preferred biomaterials are also stable under conditions used for sterilization, and additionally are stable on storage and in the course of delivery. They are also capable of flowing through a delivery cannula to an in vivo location, and being cured in situ, as by exposure to an energy source such as ultraviolet light or by chemical reaction. Thereafter the cured biomaterial is suitably amenable to shaping and contouring, by the use of conventional or custom designed arthroscopic tools or instruments. Over the course of their use in the body the cured, contoured biomaterial exhibits physical-chemical properties suitable for use in extended in vivo applications.

In a preferred embodiment, the biomaterial is a polyurethane provided as a two-part prepolymer system comprising a hydrogenated MDI isocyanate, polyethylene/polypropylene oxide polyol, and 1,4-butanediol as a chain extender. The final polymer having a hard segment content of about 30 to about 40% by weight, based on the weight of the hard segment. Thixotropic agents, such as that available under the tradename "Cab-o-sil TS-720" from Cabot can be, and preferably are, used to achieve the desired flow and pre-cure viscosity characteristics.

Optionally, and preferably, one or more catalysts are incorporated into one or more components of the biomaterial, in order to cure the biomaterial in the physiological environment within a desired length of time. Preferably, biomaterials of the present invention are able to cure (i.e., to the point where distraction means can be removed and/or other biomaterial added), within on the order of 5 minutes or less, and more preferably within on the order of 3 minutes or less.

Preferably, means are employed to improve the biostability, i.e., the oxidative and/or hydrolytic stability, of the biomaterial in vivo, thereby extending the life of the implant. See, for instance, A. Takahara, et al., "Effect of Soft Segment Chemistry on the Biostability of Segmented Polyurethanes. I. In vitro Oxidation", *J. Biomedical Materials Research,* 25:341–356 (1991) and A. Takahara, et al., "Effect of Soft Segment Chemistry on the Biostability of Segmented Polyurethanes. II. In vitro Hydrolytic Degradation and Lipid Sorption", *J. Biomedical Materials Research,* 26:801–818 (1992), the disclosures of both of which are incorporated herein by reference.

Suitable means for improving biostability include the use of an aliphatic macrodiol such as hydrogenated polybutadiene (HPDI). By judicious choice of the corresponding diisocyanate (e.g., MDI) and chain extender (e.g., ethylenediamine), those skilled in the art will be able to achieve the desired packing density, or crystallinity, of the hard segments, thereby improving the hydrolytic stability of the cured polyurethane.

Biomaterials provided as a plurality of components, e.g., a two-part polyurethane system, can be mixed at the time of use using suitable mixing techniques, such as those commonly used for the delivery of two-part adhesive formulations. A suitable mixing device involves, for instance, a static mixer having a hollow tube having a segmented, helical vein running through its lumen. A two-part polyurethane system can be mixed by forcing the respective components through the lumen, under pressure.

In a further embodiment, the static mixer can be used in a system having an application cannula, an application tip, and a cartridge having two or more chambers, each containing a separate component of the biomaterial system. A hand-powered or electrically controlled extrusion gun can be used to extrude the components through the static mixer, in order to completely mix them and thereby begin the process of curing. The biomaterial system then flows through the cannula and to the joint site or surface through the application tip. The length, diameter, and vein design of the mixing element can be varied as necessary to achieve the desired mixing efficiency.

EXAMPLE

In performing a preferred method of the present invention, the patient is brought to the pre-surgical area and prepped. Anesthesia is then induced and the area of the spine is further prepped. A small incision along the paraspinal muscles is opened under dissecting microscopic visualization. The incision typically ranges between 3 and 6 centimeters in length and is longitudinal in the plane of the spine. The paravertebral muscles are separated by blunt dissection and held apart with forceps and dividers. The intervertebral disc area is visualized, with initial exposure down to the lamina. The area below the lamina, at the point of the intervertebral foramina, can also be exposed.

The disc is examined for extruded material and any extruded material is removed. Magnetic resonance imaging ("MRI") data can be used to determine the integrity of the annulus fibrosis at this point. An arthroscope is inserted into the disc and used to examine the inside of the annulus. Optionally, an intraoperative discogram can be performed, in which a dye material is inserted and visualized in order to substantiate the integrity of the annulus fibrosis. Points of weakness, or rents, in the annulus fibrosis are identified and located and suitable means, e.g., a bioabsorbable glue is employed to block these rents.

Distraction of the intervertebral disc space can then be accomplished, as described above. Once under traction, a biomaterial, e.g., biopolymer of the present invention is introduced to the distracted space. The polymer is preferably cured over 3 to 5 minutes, and preferably within 1 to 2 minutes. The arthroscopic cannula and the application cannula are removed. The material is further allowed to harden over 15 to 20 minutes and the disc traction is removed.

The desired quantity of the curable biomaterial is delivered by minimally invasive means to the prepared site. Uncured biomaterial, either in bulk or in the form of separate reactive components, can be stored in suitable storage containers, e.g., sterile, teflon-lined metal canisters. The biomaterial can be delivered, as with a pump, from a storage canister to the delivery cannula on demand. Biomaterial can be delivered in the form of a single composition, or can be delivered in the form of a plurality of components or ingredients. For instance, biomaterial components can be separately stored and suitably mixed or combined either in the course of delivery or at the injury site itself.

In terms of its component parts, a preferred delivery system of the present invention will typically include a motor drive unit, with a remote controller, associated tube sets, a nonscope inflow delivery cannula, having independent fluid dynamics pressure and flow rate adjustments, attachments for the flush, vacuum, waste canister, and overflow jars.

The application cannula is inserted into the joint or disc space and under visualization from the fiberoptic scope the biomaterial is delivered. The flow of the biomaterial is controlled by the operator via a foot pedal connected to the pumping mechanism on the polymer canister. The biomaterial flows from the tip of the application catheter to fill the space provided.

The delivered biomaterial is allowed to cure, or cured by minimally invasive means and in such a manner that the cured biomaterial is retained in apposition to the prepared site. As described herein, the biomaterial can be cured by any suitable means, either in a single step or in stages as it is delivered. Once cured, the biomaterial surface can be contoured as needed by other suitable, e.g., endoscopic or arthroscopic, instruments. The joint is irrigated and the instruments removed from the portals.

At that point, interoperative x-rays are obtained to substantiate the preservation of the intervertebral disc space. Direct observation of the intervertebral foramina for free cursing of the nerve rootlet is substantiated by visualization. The retracted muscles are replaced and the local fascia is closed with interrupted absorbable suture. The subcutaneous fascia and skin are then closed in the usual fashion. The wound is then dressed.

As mentioned above, the cured biomaterial can be subjected to further physical/chemical modifications, e.g., in order to enhance it performance, biocompatability, biostability, and the like. For instance, calcitonin and inflammatory inhibiting molecules such as Interleuken I inhibitors can be attached to the bone composite surface to prevent local osteoporosis and local inflammatory response which may cause loosening. Similarly, the surface of the cured biomaterial can optionally be modified in order to alter, e.g., reduce, its lubricity or coefficient of friction.

Diarthroidal and Amphiarthroidal Joints

The method and biomaterials of the present invention can be used for the repair of other tissues and joints as well, including, for instance, the glenoid surface of the shoulder, the first carpometacarpal joint of the hand, the knee, the hip, the hallux joint, the temporal mandibular joint, the subtalar joint in the ankle, the other metatarsal phalangeal joints of the feet.

With respect to the shoulder, for instance, a common situation arises in the elderly patient who has a degenerated rotator cuff. Usually, such patients have lost the superior portion of the rotator cuff with the complete loss of the supraspinatus tendon. Often they also have a superior riding of the humerus so that it articulates very high on the glenoid and with any abduction there is significant impingement on the acromium process.

Using the approach presently described, a biomaterial can be delivered, cured, and attached to the glenoid, all using minimally invasive means, in order to resurface the glenoid surface and extend up over the superior portion of the humerus. There the cured biomaterial will act as a spacer between the humerus and the acromium process. Resurfacing the underside of the acromium and the glenoid with a single structure that allows the humerus to be spaced down from the acromium process and to avoid impingement on the acromium with abduction.

Other areas of the body that will also benefit from the creation of a spacer, yet do not involve significant weight-bearing constraints, include the first carpometacarpal joint of the hand, the radialhumeral joint. The method of the present invention can be used to provide a spacer that will allow motion with a minimum of friction, while also providing desired mechanical stability to the area.

Yet other applications include repair of the first carpometacarpal joint, which is another diarthroidal joint. The carpal bone and the base at the metacarpal are normally covered with articular cartilage. This joint, however, is subject to significant degenerative change over time because of stresses that are placed on it by normal hand motion. These stresses can result in a narrowing of the joint space and eventually a bone-on-bone situation, with marked loss of motion and significant. Such a joint can be repaired by minimally invasive means using the method of the present invention, e.g., by placing an appropriate spacer of biomaterial through the arthroscope and affixing it to one side or the other of the joint.

In such a procedure, two small holes can be drilled into the base of the metacarpal, for instance. Curable biomaterial can then be applied into those anchor points and over the surface of the base of the metacarpal. The final cured biomaterial provides both a cushioning and a spacing function, which will serve to decrease pain and improve motion and function.

Yet another joint that is amenable to repair using the present method is the hallux joint, also known as the metatarsal phalangeal joint. In a condition called hallux rigiditus, the cartilage between the base of the 1st phalanx and the end of the first metatarsal has degenerated and there are significant bony spurs forming due to the degeneration of the cartilage. As with the first carpometacarpal joint at the wrist, the method of this invention can involve arthroscopically drilling a plurality of small holes in the head of the metatarsal and delivering and curing a biomaterial to produce the needed cushioning and spacing.

Yet other areas of application include the fibrocartilage of the temporal mandibular joint, costochondral junctions, and the acromioclavicular joint. Another application involves the subtalar joint in the ankle. This is a common area for medial subluxation of the ankle in the patient with rheumatoid arthritis who gets stretching and weakening of the tibialis posterior tendon and instability at the medial aspect of the ankle, resulting in persistent ankle pain. A biomaterial and method of the present invention can be used to build up the subtalar joint area in order to realign the ankle and correct the eversion of the foot, thereby obviating the need for an ankle fusion.

The foregoing description is intended to be illustrative of the invention, but is not to be considered as comprehensive or limiting of its scope.

What is claimed is:

1. An apparatus for repairing a damaged or diseased intervertebral disc, the apparatus comprising a mold apparatus positioned within the intervertebral disc and comprising an inflated balloon containing a cured biomaterial, the apparatus being formed by a method that comprises the steps of:
   a) using minimally invasive techniques to remove damaged or diseased nucleus from the disc;
   b) providing a mold apparatus comprising a balloon adapted to contain a biomaterial and a delivery cannula adapted to flowably connect a biomaterial source to the balloon, and using minimally invasive means to position the balloon within the disc;
   c) providing a biomaterial source comprising a polyurethane system comprising a plurality of components adapted to be mixed at the time of use to provide a flowable biomaterial and initiate its cure; mixing the biomaterial components upon positioning of the balloon; and using minimally invasive techniques to deliver the flowable biomaterial by injection into the balloon under pressure sufficient to provide on the order of 3 atmospheres to on the order of 4 atmospheres pressure to distract the disc space, and
   d) allowing the delivered biomaterial to cure within 5 minutes of mixing the components to permit the cannula to be removed and to provide a permanent replacement for the nucleus,
   wherein the polyurethane system comprises a two-part prepolymer system and further comprises an isocyanate reactant consisting essentially of aromatic isocyanates, the method further comprising the further step of deflating the balloon as biomaterial is delivered.

2. An apparatus for repairing a damaged or diseased intervertebral disc, the apparatus comprising a mold apparatus positioned within the intervertebral disc and comprising an inflated balloon containing a cured biomaterial, the apparatus being formed by a method that comprises the steps of:
   a) using minimally invasive techniques to remove damaged or diseased nucleus from the disc;
   b) providing a mold apparatus comprising a balloon adapted to contain a biomaterial and a delivery cannula adapted to flowably connect a biomaterial source to the balloon, and using minimally invasive means to position the balloon within the disc;
   c) providing a biomaterial source comprising a polyurethane system comprising a plurality of components adapted to be mixed at the time of use to provide a flowable biomaterial and initiate its cure; mixing the biomaterial components upon positioning of the balloon; and using minimally invasive techniques to deliver the flowable biomaterial by injection into the balloon under pressure sufficient to provide on the order of 3 atmospheres to on the order of 4 atmospheres pressure to distract the disc space, and d) allowing the delivered biomaterial to cure within 5 minutes of mixing the components to permit the cannula to be removed and to provide a permanent replacement for the nucleus, wherein a) the polyurethane system comprises a two-part prepolymer system and further comprises an isocyanate reactant consisting essentially of aromatic isocyanates, b) the minimally invasive steps are performed using arthroscopic or endoscopic techniques including visualization, and c) the method comprises the further step of deflating the balloon as biomaterial is delivered.

3. An apparatus for repairing a damaged or diseased intervertebral disc, the apparatus comprising a mold apparatus positioned within the intervertebral disc and comprising an inflated balloon containing a cured biomaterial, the apparatus being formed by a method that comprises the steps of:

a) using minimally invasive techniques to remove damaged or diseased nucleus from the disc;

b) providing a mold apparatus comprising a balloon adapted to contain a biomaterial and a delivery cannula adapted to flowably connect a biomaterial source to the balloon, and using minimally invasive means to position the balloon within the disc;

c) providing a biomaterial source comprising a polyurethane system comprising a plurality of components adapted to be mixed at the time of use to provide a flowable biomaterial and initiate its cure; mixing the biomaterial components upon positioning of the balloon; and using minimally invasive techniques to deliver the flowable biomaterial by injection into the balloon under pressure sufficient to provide on the order of 3 atmospheres to on the order of 4 atmospheres pressure to distract the disc space, and d) allowing the delivered biomaterial to cure within 5 minutes of mixing the components to permit the cannula to be removed and to provide a permanent replacement for the nucleus, wherein the polyurethane system comprises a two-part prepolymer system and further comprises an isocyanate reactant consisting essentially of aromatic isocyanates, comprising the further step of deflating the balloon as biomaterial is delivered, and wherein the cured biomaterial provides a heterogeneous implant having a plurality of regions.

4. An apparatus according to claim 3 wherein the regions comprise a more rigid outer region and a more flexible inner region.

5. An apparatus for repairing a damaged or diseased intervertebral disc, the apparatus comprising a mold apparatus positioned within the intervertebral disc and comprising an inflated balloon containing a cured biomaterial formed by a method that comprises the steps of:

a) using minimally invasive techniques to remove damaged or diseased nucleus from the disc;

b) providing a mold apparatus comprising a balloon adapted to contain a biomaterial and a delivery cannula adapted to flowably connect a biomaterial source to the balloon, and using minimally invasive means to position the balloon within the disc;

c) providing a biomaterial source comprising a polyurethane system comprising a plurality of components adapted to be mixed at the time of use to provide a flowable biomaterial and initiate its cure; mixing the biomaterial components upon positioning of the balloon; and using minimally invasive techniques to deliver the flowable biomaterial by injection into the balloon under pressure sufficient to provide on the order of 3 atmospheres to on the order of 4 atmospheres pressure to distract the disc space, and d) allowing the delivered biomaterial to cure within 5 minutes of mixing the components to permit the cannula to be removed and to provide a permanent replacement for the nucleus, wherein a) the polyurethane system comprises a two-part prepolymer system and further comprises an isocyanate reactant consisting essentially of aromatic isocyanates, b) the minimally invasive steps are performed using arthroscopic or endoscopic techniques including visualization, and c) the method comprises the further step of deflating the balloon as biomaterial is delivered, and wherein the cured biomaterial provides a heterogeneous implant having a plurality of regions.

6. An apparatus according to claim 5 wherein the regions comprise a more rigid outer region and a more flexible inner region.

* * * * *